US00PP17555P2

(12) United States Plant Patent
Grueber

(10) Patent No.: US PP17,555 P2
(45) Date of Patent: Apr. 3, 2007

(54) ***EUPHORBIA* PLANT NAMED 'INNEUPHHEL'**

(50) Latin Name: *Euphorbia hybrida*
Varietal Denomination: Inneuphhel

(75) Inventor: Garry Grueber, Mainz (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 11/236,747

(22) Filed: Sep. 27, 2005

(51) Int. Cl.
*A01H 5/00* (2006.01)

(52) U.S. Cl. ..... Plt./302
(58) Field of Classification Search ..... Plt./302
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Euphorbia* plant named 'Inneuphhel', characterized by its compact and mounded plant habit; freely branching habit; red-colored developing foliage and green and pale yellow variegated mature foliage; resistance to Powdery Mildew; and good garden performance.

1 Drawing Sheet

Botanical designation: *Euphorbia hybrida.*
Cultivar denomination: 'Inneuphhel'.

BACKGROUND OF THE INVENTION

The present Invention relates to a new and distinct cultivar of *Euphorbia* plant, botanically known as *Euphorbia hybrida,* and hereinafter referred to by the cultivar name Inneuphhel.

The new *Euphorbia* is a naturally-occurring branch mutation of the *Euphorbia hybrida* cultivar Efanthia, not patented. The new *Euphorbia* was discovered and selected from within a population of plants of the cultivar Efanthia in a controlled environment in Gensingen, Germany in May, 2000.

Asexual reproduction of the new cultivar by terminal vegetative cuttings since May, 2001 in Gensingen, Germany has shown that the unique features of this new *Euphorbia* are stable and reproduced true to type in successive generations.

SUMMARY OF THE INVENTION

Plants of the cultivar Inneuphhel have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Inneuphhel'. These characteristics in combination distinguish 'Inneuphhel' as a new and distinct cultivar:

1. Compact and mounded plant habit.
2. Freely branching habit.
3. Red-colored developing foliage and green and pale yellow variegated mature foliage.
4. Resistance to Powdery Mildew.
5. Good garden performance.

In side-by-side comparisons conducted in Gensingen, Germany, plants of the new *Euphorbia* differed primarily from plants of the parent, the cultivar Efanthia in the following characteristics:

1. Plants of the new *Euphorbia* grew slower than plants of the cultivar Efanthia.
2. Plants of the new *Euphorbia* had green and pale yellow variegated leaves whereas plants of the cultivar Efanthia had green-colored leaves.

Plants of the new *Euphorbia* can be compared to plants of the *Euphorbia* cultivar Imprefant, disclosed in U.S. Plant Pat. No. 16,908. In side-by-side comparisons conducted in Gensingen, Germany, plants of the new *Euphorbia* differed from plants of the cultivar Imprefant in the following characteristics:

1. Plants of the new *Euphorbia* grew slower than plants of the cultivar Imprefant.
2. Plants of the new *Euphorbia* had green and pale yellow variegated leaves whereas plants of the cultivar Imprefant had burgundy-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Euphorbia.*

The photograph at the top of the sheet is a close-up view of typical leaves of 'Inneuphhel'.

The photograph at that bottom of the sheet comprises a side perspective view of a typical plant of 'Inneuphhel' grown in a container.

DETAILED BOTANICAL DESCRIPTION

The aforementioned photographs and following observations and measurements describe plants grown in Bonsall, Calif., in an outdoor nursery during the spring and summer under full sun conditions with day temperatures ranging from 10° C. to 32° C. and night temperatures ranging from 2° to 21° C. After planting rooted cuttings, plants were grown for about 17 weeks with three plants per gallon containers. Plants were pinched one time. Color references are made to The Royal Horticultural Society Colour Chart, 1995 Edition, except where general terms of ordinary dictionary significance are used.

Botanical classification: *Euphorbia hybrida* cultivar Inneuphhel.

Parentage: Naturally-occurring branch mutation of the *Euphorbia hybrida* cultivar Efanthia, not patented.

Propagation:

*Type.*—By cuttings.

*Time to initiate roots, summer.*—About 14 days at 20° C.

*Time to initiate roots, winter.*—About 18 days at 20° C.

*Time to develop roots.*—About 20 days at temperatures of 20° C.

*Root description.*—Fine, white in color.

*Rooting habit.*—Freely branching.

Plant description:

*Plant form and growth habit.*—Compact and mounded plant habit; plants mostly upright; inverted triangle; perennial subshrub. Moderate growth rate.

*Branching habit.*—Freely branching, usually about ten lateral branches develop per plant; dense and bushy plant form.

*Plant height.*—About 23 cm.

*Plant diameter* (*single plant*).—About 23 cm.

*Lateral branch description.*—Length: About 15 cm. Diameter: About 3 mm. Internode length: About 8 mm. Strength: Strong. Texture: Pubescent. Color: Young stems, 146C; mature stems, 185A.

Foliage description:

*Arrangement.*—Alternate to whorled; simple.

*Length.*—About 5.3 cm.

*Width.*—About 1.4 cm.

*Shape.*—Elliptical.

*Apex.*—Acute.

*Base.*—Attenuate.

*Margin.*—Entire.

*Texture, upper and lower surfaces.*—Pubescent.

*Venation.*—Pinnate, arcuate.

*Color.*—Developing foliage, upper surface: 144A, towards the margins, 145C; overlain with close to 53A. Developing foliage, lower surface: 147C overlain with close to 53A. Fully developed foliage, upper surface: Center, 147B; towards the margins, 22D; at the margin, 48A. Mature foliage, lower surface: Center, 148B; towards the margins, 10C; at the margin 48A. Venation, upper surface: 147C. Venation, lower surface: 148D.

*Petiole.*—Length: About 7 mm. Diameter: About 2 mm. Texture, upper and lower surfaces: Pubescent. Color, upper surface: 147D. Color, lower surface: 147C.

Flower description: Flower development has not been observed on plants of the new *Euphorbia*.

Disease/pest resistance: Plants of the new *Euphorbia* have been observed to be resistant to Powdery Mildew. Plants of the new *Euphorbia* not been observed to be resistant to pests and other pathogens common to *Euphorbia*.

Temperature tolerance: Plants of the new *Euphorbia* are tolerant to temperatures as low as −6° C. and as high as 40° C.

It is claimed:

1. A new and distinct *Euphorbia* plant named 'Inneuphhel', as illustrated and described.

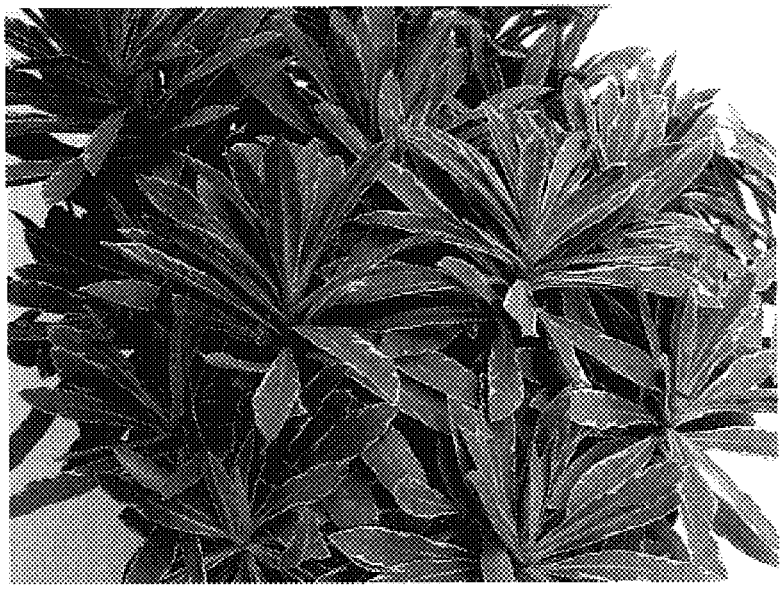
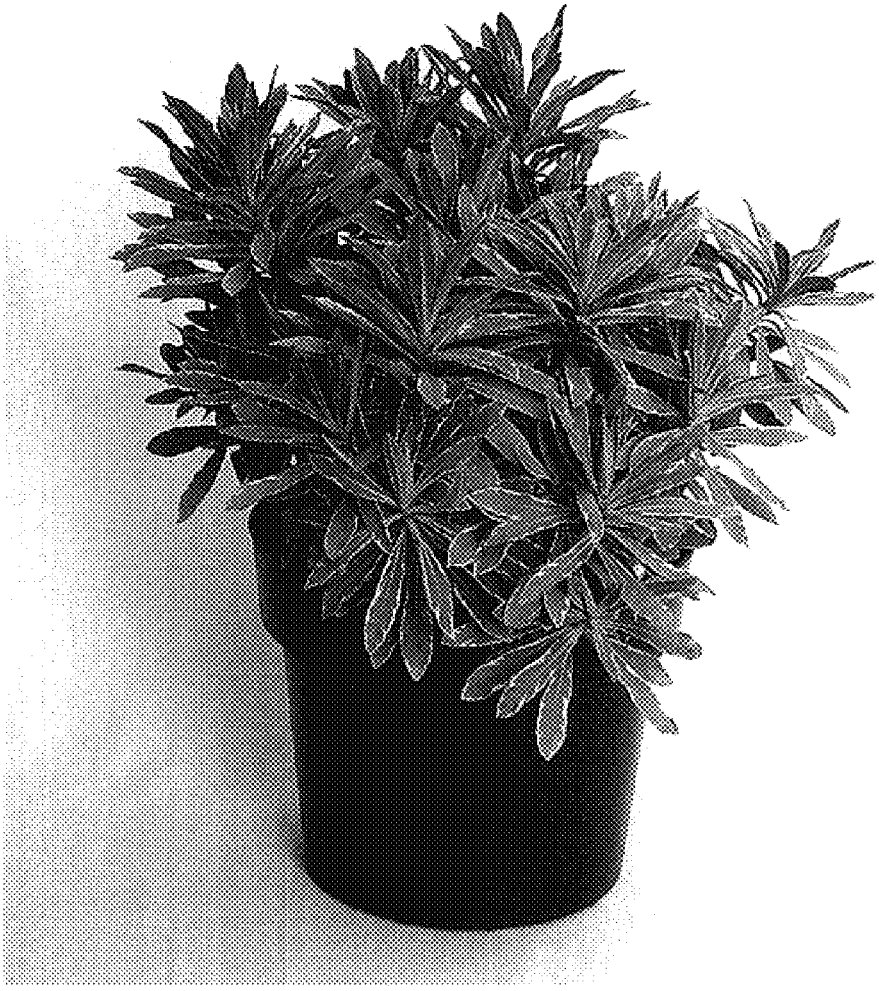

* * * * *